United States Patent
Bell-Greenstreet

(10) Patent No.: US 7,226,431 B1
(45) Date of Patent: Jun. 5, 2007

(54) LOW-COST NON-REUSABLE AND ANTI-NEEDLESTICK ENHANCEMENTS TO DISPOSABLE SYRINGES

(76) Inventor: Daryl L. Bell-Greenstreet, P.O. Box 437, Lakeside, CA (US) 92040

( * ) Notice: Subject to any disclaimer, the term of this patent is extended or adjusted under 35 U.S.C. 154(b) by 8 days.

(21) Appl. No.: 11/330,374

(22) Filed: Jan. 11, 2006

Related U.S. Application Data

(60) Provisional application No. 60/646,567, filed on Jan. 25, 2005.

(51) Int. Cl.
*A61M 5/00* (2006.01)
(52) U.S. Cl. .................................... 604/110
(58) Field of Classification Search ............. 604/110, 604/181, 187, 165, 218, 192–198, 214, 221, 604/222, 228, 223; 128/919
See application file for complete search history.

(56) References Cited

U.S. PATENT DOCUMENTS

| | | | | |
|---|---|---|---|---|
| 4,713,056 A * | 12/1987 | Butterfield | ............ | 604/110 |
| 4,973,309 A * | 11/1990 | Sultan | ............ | 604/110 |
| 5,078,686 A * | 1/1992 | Bates | ............ | 604/110 |
| 5,135,512 A * | 8/1992 | Mazurik et al. | ............ | 604/228 |
| 5,226,882 A * | 7/1993 | Bates | ............ | 604/110 |
| 5,242,416 A * | 9/1993 | Hutson | ............ | 604/192 |
| 5,259,841 A * | 11/1993 | Hohendorf et al. | ............ | 604/110 |
| 5,554,122 A * | 9/1996 | Emanuel | ............ | 604/110 |
| 5,891,098 A * | 4/1999 | Huang | ............ | 604/164.08 |
| 6,077,245 A | 6/2000 | Heinrich et al. | | |
| 6,322,540 B1 * | 11/2001 | Grabis et al. | ............ | 604/198 |
| 2002/0035350 A1 | 3/2002 | Turnbull et al. | | |
| 2005/0096601 A1* | 5/2005 | Doyle | ............ | 604/198 |

* cited by examiner

*Primary Examiner*—Matthew F. DeSanto

(57) ABSTRACT

A disposable syringe incapable of re-use comprising a plunger itself comprising an elongated stem, a disk called a "spider" held near the lower end of the stem. The plunger furthermore comprises a stem extension in the shape of a short cylinder, affixed to the lower face of the spider. Finally the plunger comprises a handle affixed to the upper end of the stem. In addition, the syringe comprises a lower seal and upper seal both of cylindrical annular shape made of rubbery material, having their external cylindrical surface forming an air-tight fit with the inner wall of the barrel. The internal cylindrical surface of the lower seal forms a liquid-tight slip fit with the stem extension. The upper seal's internal diameter is larger than the stem thus forming a gap between itself and the stem, this gap allowing fluid to circulate freely. In addition, the upper seal forms an air-tight combination with the spider when they are in contact. In the syringe's initial operational state, the lower seal, the plunger and the upper seal are located at the bottom of the barrel. As the syringe reaches its final state, it becomes unusable for any subsequent use because the lower seal cannot be drawn upward and the upper seal is abandoned and remains at the top of the barrel.

21 Claims, 8 Drawing Sheets

LOW-COST NON-REUSABLE AND ANTI-NEEDLESTICK ENHANCEMENTS TO DISPOSABLE SYRINGES

This invention claims the benefit of U.S. Provisional Application No. 60/646,567 with the title. "Low-Cost Non-Reusable Disposable Syringe with Anti-Needlestick Protection" filed on Jan. 25, 2005 and which is hereby incorporated by reference. Applicant claims priority pursuant to 3.5 U.S.C. Par 119(e)(i). This invention relates to syringe technology designed to reduce the risk of spreading infection and fighting intravenous drug abuse due to improper syringe re-use. The invention relates more specifically to features of syringes that make them disposable and non-reusable, and to features of syringes to equip them with tamper resistance and anti-needlestick protection.

FIELD OF THE INVENTION

Background

The spread of diseases through the practice of sharing and re-using of unsterilized needles and syringes is significant in the non-professional setting. Replacing conventional re-usable syringes with syringes that are disposable and can be used only once can eliminate this practice. The primary merit of this invention is that it removes from the user, and anyone else who may acquire the syringe, the ability to determine whether or not it will be re-used. One of the most important factors in performing this replacement successfully is the cost of manufacturing such syringes. While the prior art abounds with patents describing disposable syringes and one-use syringes, the cost of such syringes often prevents their widespread employment. That cost must be brought down with simpler designs. There is an urgent need for a very simple, yet very reliable, low cost, non-reusable, tamper resistant, anti-needle stick disposable syringe.

The spread of diseases and accidents through inadvertent needlestick is also of concern and should be addressed in the design of any syringe, be it reusable or non-reusable.

The most relevant patent documentation is US application 2002/0035350 by Turnbull et al. The plunger of the syringe comprises an annular rear valve, and an annular front valve both of which form a liquid-tight seal with the interior of the barrel. The annular front valve and the annular rear valve are traversed by the plunger. The plunger is shaped such that when it is pushed forward it forms a water-tight seal with the front valve. Similarly, it is also shaped to form a water-tight seal with the rear valve when it is retracted. Therefore, when the plunger is pulled back, the seal between the barrel and the rear valve closes and a partial vacuum is formed inside the front part of the barrel. Because of this partial vacuum, liquid can be drawn into the syringe. As the plunger is pulled back it also mechanically draws backward the front valve because shoulders mounted on the plunger engage shoulders mounted on the front valve. Unfortunately, at this time some of the liquid heretofore trapped in the front part of the barrel escapes into the mechanism and is thereby wasted. When the plunger is subsequently pushed forward the seal between the front valve and the plunger closes, thus forcing the remainder of the liquid out of the syringe. However, the rear valve is left behind, and becomes useless for a second operation. A bypass opening in the plunger allows air to flow from the back to the front during a second retraction operation to prevent a vacuum from forming in the front of the syringe and thus disabling the function of the syringe. Unfortunately, it does nothing to prevent an abuser from re-introducing a liquid into the syringe from a pressurized vial. Turnbull et al's invention is wasteful of medication and its non-reusability feature can be easily defeated. Thus there is still a need for an inexpensive, simple, safe, non-wasteful and more secure non-re-usable disposable syringe.

Further features, aspects, and advantages of the present invention over the prior art will be more fully understood when considered with respect to the following detailed description claims and accompanying drawings.

SUMMARY OF THE INVENTION

The present invention describes a disposable syringe incapable of re-use regardless of the user's intent consisting of a non-reuse mechanism, anti-needlestick protection, and tamper resistance features to be added to disposable syringes to render them safer for public use.

This syringe comprises a barrel in the shape of a hollow cylinder, having its upper end open and equipped on the outside with finger gripping devices positioned and shaped to be gripped with two fingers for better handling, and terminated at its lower end with a needle cap holding a medical injection needle.

The syringe also comprises a plunger in slidable contact with the inside surface of the barrel. This plunger comprises an elongated stem substantially concentric with the barrel. The plunger also comprises a disk called a "spider" held by the stem near the lower end of the stem. The spider is perpendicular to the axis of, and axially centered with, the stem, and forms a loose fit with the inside surface of the barrel. The plunger furthermore comprises a stem extension in the shape of a short cylinder of predetermined length and diameter, affixed to the lower face of the spider and axially centered with the stem. Finally the plunger comprises a handle affixed to upper end of the stem.

In addition, the syringe comprises a lower seal of cylindrical annular shape made of rubbery material, having its external cylindrical surface forming an air-tight fit with the inner wall of the barrel. The internal cylindrical surface of the lower seal forms a liquid-tight slip fit with the stem extension. This combination is henceforth called the lower liquid-tight combination.

Furthermore the syringe comprises an upper seal of cylindrical annular shape made of rubbery material, having its external cylindrical surface forming an air-tight fit with the inner wall of the barrel. This upper seal's internal diameter is larger than the stem thus forming a gap between itself and the stem, this gap allowing fluid to circulate freely. In addition, the upper seal has its lower surface that conforms to the upper surface of the spider, thereby forming an air tight combination when the spider and the upper seal are in contact. This combination is henceforth called the upper air-tight combination.

The operation of the syringe requires that its initial state be such that the lower seal, the plunger and the upper seal are all located all the way down the barrel thus forming the lower air-tight combination and the upper air-tight combination. Upon first use of the syringe, the plunger is pulled up thus drawing up the spider which pulls the upper seal upward thereby creating a primary vacuum below the upper seal, and above the lower seal. This primary vacuum pulls the lower seal upward, thereby drawing liquid into the syringe through the needle.

When the plunger is pushed downward the spider pushes down the lower seal, thereby expelling the liquid from the syringe until the spider and the lower seal reach the bottom of the syringe. Furthermore the upper seal is abandoned near the top of said barrel.

As the syringe reaches its final state, it becomes unusable for any subsequent use because the upper seal is abandoned near the top of the barrel, the primary partial vacuum is irretrievably broken and the lower seal cannot be drawn upward by pulling on the plunger.

Many variations exist: the plunger can comprise a molded piece that includes the stem and any combination of the spider, the stem extension and the handle. The spider can comprise indentations on its periphery to facilitate the flow of fluids. The upper and lower seals can be 180 degrees reversible in orientation with respect to the axis of said syringe and can also be identical to facilitate manufacturing.

The upper seal and lower seals can carry ribs on their outer surface in contact with the inner wall of the barrel. Adjusting the number and cross-sectional shape of the ribs can be being used to control the amount of friction the upper and lower seal have with the inner wall of the barrel. A slant in the rib's cross section shape can be generated by the frictional force between the ribs and the inner wall of the barrel, and this slant can produce upon a change in the direction of motion, a sharp increase in the frictional force which can facilitate the abandonment of the upper seal as the plunger is pushed down.

The stem extension can be made slightly shorter than the lower seal to ensure that as the plunger is pushed all the way to the bottom the lower seal is compressed and all the liquid in the syringe is completely expelled.

The barrel can be made of transparent or translucent material to facilitate inspection of its content and it can be made of tempered material to discourage tampering. The needle can be annealed at its base to discourage its removal.

Manufacturing of the handle can be simplified by forming a molded billet in the upper end of the stem, inserting the upper seal and then flattening the billet into a flat flexible handle. Alternatively, a flat disc button can be affixed at the upper end of the stein, perpendicularly to the axis of the syringe.

Tampering can be prevented by crimping the barrel near its upper end.

Safety of use of the syringe can be enhanced by means of an anti-needlestick sleeve essentially the shape of a hollow cylindrical body made of flexible transparent material loosely fitting over the barrel, and which can be slid from a retracted position to an extended position. A set of holes cut in this anti-needlestick sleeve are used to control its movement. These include a retaining hole, a guide slot cut in the longitudinal direction, and a latching hole. The barrel comprises on its outer surface a set of protuberances matching the holes in the sleeve. These include a retaining detent matching in location the retaining hole when the anti-needlestick sleeve is in a retracted position; a guide detent matching in location the guide slot; and a latching detent, matching in location the latching hole when the anti-needlestick sleeve is in an extended position.

The combination of the retaining detent and retaining hole keeps the anti-needlestick sleeve in the retracted position before and during use, thus exposing the needle. The flexibility of the anti-needlestick sleeve allows it to be compressed from a circular cylindrical shape to an oval cylindrical shape, thus allowing the release of the retaining hole from the retaining detent by the application of sideways pressure. The combination of the guide detent and guide slot constrains the movement of the anti-needlestick sleeve to a longitudinal direction with respect to the syringe, and allows the anti-needlestick sleeve to be slid from the retracted position to the extended position thus shielding the needle. The combination of the latching hole and the latching detent keeps the anti-needlestick sleeve in a permanent extended latched position after use, thus shielding the needle and preventing it from being exposed again.

Assembly can be simplified by making the anti-needlestick sleeve is 180 degrees reversible with respect to the axis of the syringe, and with respect to the retaining hole, the guide slot and the latching hole, thereby facilitating assembly. The retaining detent can be cabochon-shaped to facilitate its release. The latching detent can be rectangular in cross section to make it more difficult to be unlatched.

The anti-needlestick sleeve allows the syringe to be utilized and disposed in a waste disposal system not necessarily designed for hazardous materials.

Further features, aspects, and advantages of the present invention will be more fully understood when considered with respect to the following detailed description claims and accompanying drawings.

DESCRIPTION OF PREFERRED EMBODIMENTS

Figure 1:
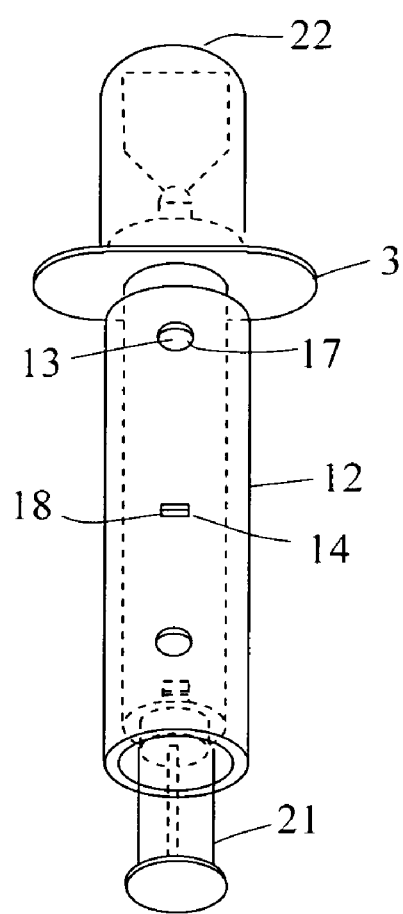
FIG. 1 represents an assembled syringe including the anti-needlestick sleeve and the needle and handle caps.

The present invention describes improvements to a disposable syringe that is normally used to draw a medicament from a vial and inject this medicament into a patient. The improvements render the syringe non-reusable, tamper resistant and provide protection against accidental needle stick. The improvements comprise the following components:

a) a plunger, comprised of a main stem of the plunger, a spider of the plunger, an expanded stem extension of the plunger, and a billet of the plunger, which becomes the handle of the plunger;

b) a plunger assembly, also known as the non-reuse mechanism, comprised of a lower seal, an upper seal, and the plunger (as listed above);

c) a hollow tempered barrel, with an annealed needle, lobes, retaining detent, latching detent, guide detent, and a tamper resistant closure; and d) an anti-needlestick sleeve, with a guide slot, a retaining hole, and latching hole.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further application of the principles of the invention as illustrated therein being contemplated as would normally occur to one skilled in the art to which the invention relates.

Figure 1A:
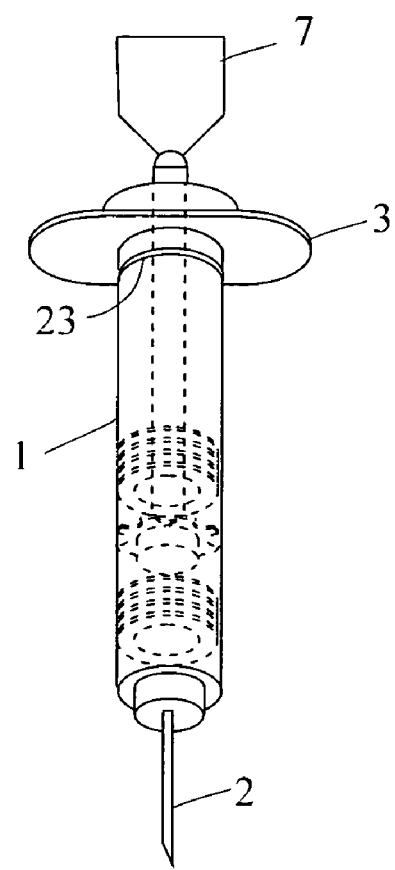
FIG. 1A describes the assembled syringe without the anti-needlestick sleeve and the needle and handle caps.
Figure 2:
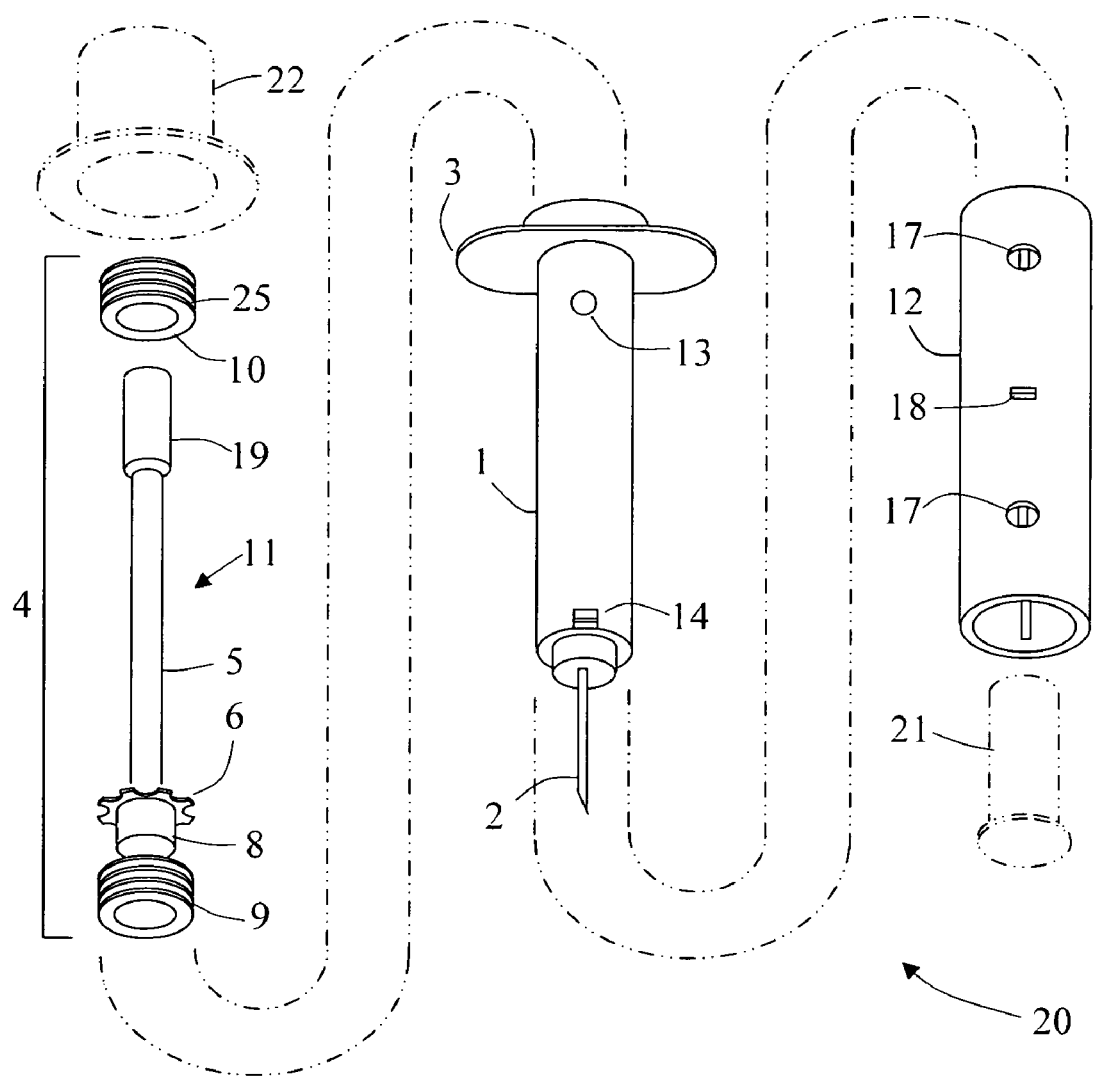
FIG. 2 is an exploded front view of the syringe with all its components, before assembly.
Figure 2A:
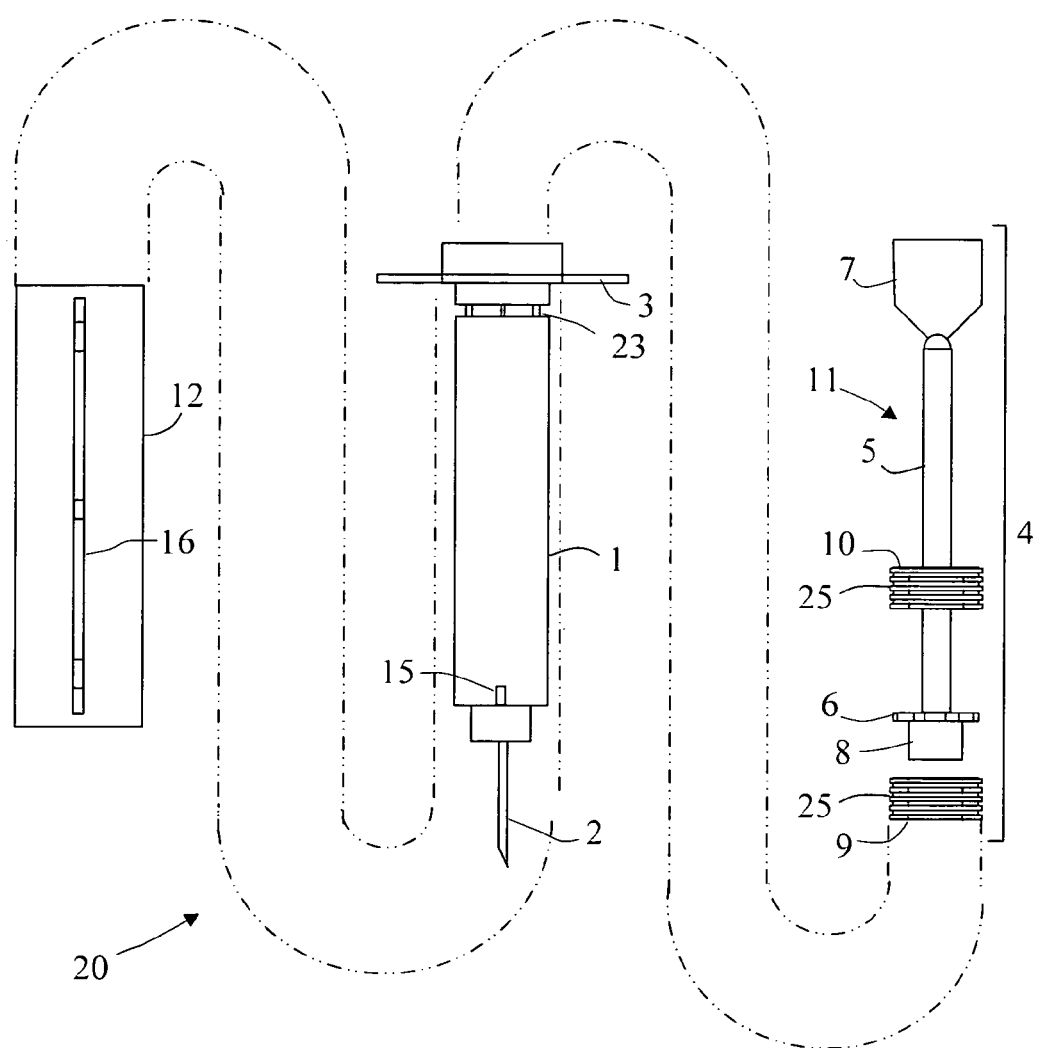
FIG. 2A is an exploded rear view of the syringe with all its components, after assembly, and with caps removed.

A preferred embodiment is shown in FIG. 1 and FIG. 1A with and exploded view shown in FIG. 2, and the reverse side exploded view in FIG. 2A. The barrel 1 is commonly insertion molded, having an injection needle 2 affixed in the bottom, and an open-ended top surrounded with finger gripping means, such as, but not limited to, lobes 3. The barrel 1 is typically made of a transparent material.

Plungers are commonly molded as a single part. The plunger 11 is longer than the barrel 1. The plunger 11 is terminated at the lower end by a stem extension 8 of a diameter that is larger than the main stem 5, followed by a spider 6, and at the upper end of the main stem 5, by a billet 19 that can be fabricated to form a handle. The spider 6 has a diameter only slightly smaller than the inner diameter of the barrel 1. spider includes gaps on it periphery to allow fluid to circulate freely when the syringe is used more then once. These can be in the form of indentations located at the periphery of said spider. The location on the periphery between indentations forms a loose fit with the inner wall of the barrel. Thus the plunger 11 alone slides effortlessly along the barrel 1 offering no resistance to air or liquid circulation within the barrel 1. The expanded stem extension 8 extends below the spider 6 where it almost completely traverses the rubber-like lower seal 9. The main stem 5 above the spider traverses a rubber-like upper seal 10. The plunger 11 is made of rigid material, such as, but not limited to, thermoplastic or metal.

Optionally, the spider may carry on its periphery a series of indentations designed to center the spider along the axis of the syringe and to allow fluids to flow by.

The lower seal 9 will initially be located in the bottom of the barrel 1. It slip-fits around the stem extension 8 and will be beneath the spider 6. This lower seal 9, which will not be mechanically connected to the plunger, forms an air-tight fit with the inner wall of the barrel 1. This air-tight fit creates a pre-determinable resistance to longitudinal movement within the barrel 1. The lower seal 9 also forms a liquid tight slip fit connection with the stem extension 8. It is almost completely traversed by the stem extension 8. The stem extension 8 is shorter than the lower seal 9 to prevent wastage of medicine. The difference in length can range from 0.002 inches to 0.020 inches.

Because of the liquid tight slip fit, the lower seal 9 and bottom face of the stem extension 8 form a liquid-tight surface across the bottom of the plunger assembly 4. The lower seal 9 forms a mating surface and a liquid-tight fit with the bottom of the spider 6. The plunger assembly 4 consists of the combination of the plunger 11, the upper seal 10, and the lower seal 9.

The upper seal 10 will be traversed by the main stem 5 and is located above the spider 6. The upper seal 10 forms an air-tight fit with the inner wall of the barrel 1. The upper surface of the spider 6 and the lower surface of the upper seal 10 conform to each other to form a mating, air-tight surface when the spider 6 and the upper seal 10 are in contact. However, because the inner diameter of the upper seal 10 is significantly larger than the diameter of the main stem 5, the upper seal 10 does not form any fit with the main stem 5 and air is able to circulate freely between them.

Optionally, the lower seal 9 and upper seal 10 can carry on their outer surface in contact with the inner wall of the barrel 1 a series of ribs 25, the number and cross-sectional shape of which can be used to control the amount of friction the seal and the inner wall of said barrel. A slant may be in their cross section shape can be generated by the frictional force between the ribs and the inner wall of said barrel. This slant can produce a sharp increase in the frictional force upon a change in the direction of motion of the plunger 11. This sharp increase in the frictional force can be used to facilitate the abandonment of the upper seal 10 near the top of the barrel 1.

Both the upper seal 10 and the lower seal 9 are longitudinally symmetrical to facilitate ease of assembly, by being reversible. Both seals are made of a flexible material such as, but not limited to, rubber or silicone rubber. Both seals can be identical to simplify manufacturing.

Optionally a vacuum may be established at manufacturing time between the lower seal 9 and the upper seal 10 to supplement the hand generated vacuum obtained during the operation of the syringe as shall be discussed below.

As shown in FIG. 1 and FIG. 2 the anti-needlestick sleeve 12 is made of thin, flexible transparent material, which surrounds the barrel 1 of the syringe 20. The anti-needlestick sleeve's 12 anchorage to the barrel 1 is governed by two protuberances on the outside wall of the barrel 1, which are shown in FIG. 2: the cabochon-shaped retaining detent 13 and the latching detent 14. The latching detent 14 has a rectangular cross-section. The sleeve 12 is equipped with at least one retaining hole 17 that latches onto the retaining detent 13 in its initial condition. The latching hole 18 latches to the latching detent 14 upon deployment of the anti-needlestick sleeve. The anti-needlestick sleeve 12 is made of transparent material, allowing any markings on the barrel 1 to be clearly read and the medication in the syringe 20 to be clearly visible when covered by the sleeve 12.

A needle cap 21 and a plunger cap 22 are used to shield the needle 2 and the handle respectively before use. They are usually shipped with the syringe 20 as shown in FIG. 2, and are typically discarded before use of the syringe.

Shown in FIG. 2A, is mostly the reverse exploded view of the invention. This shows the upper seal 10 where it traverses the main stem 5 of the plunger. Also shown here is the billet (shown in FIG. 2 as billet 19) after it has been fabricated into handle 7. During manufacturing, the billet is flattened into thin flexible handle by the same rotary tool and at the same time as the barrel is crimped closed. FIG. 1A and FIG. 2A also shows the guide detent 15 and the guide slot 16. The purpose of the guide detent 15 and guide slot 16 is to assure purely longitudinal movement of the anti-needlestick sleeve 12. The barrel 1 is shown after the application of the tamper resistant closure 23.

The anti-needlestick sleeve is 180 degrees reversible with respect to the axis of the syringe, and with respect to the retaining hole, guide slot and latching hole, thereby facilitating assembly.

The tamper resistant closure 23 is a means for providing tamper resistance by closing the upper end of barrel 1. Closure can be accomplished by such means as, but not limited to, crimping, after the plunger assembly has been inserted. The closure 23 aids in the prevention of tampering with the non-reuse mechanism. Below the closure 23 sufficient room is provided for the longitudinal motion of the plunger and to fill the graduated section of barrel 1 with liquid.

Figure 3:
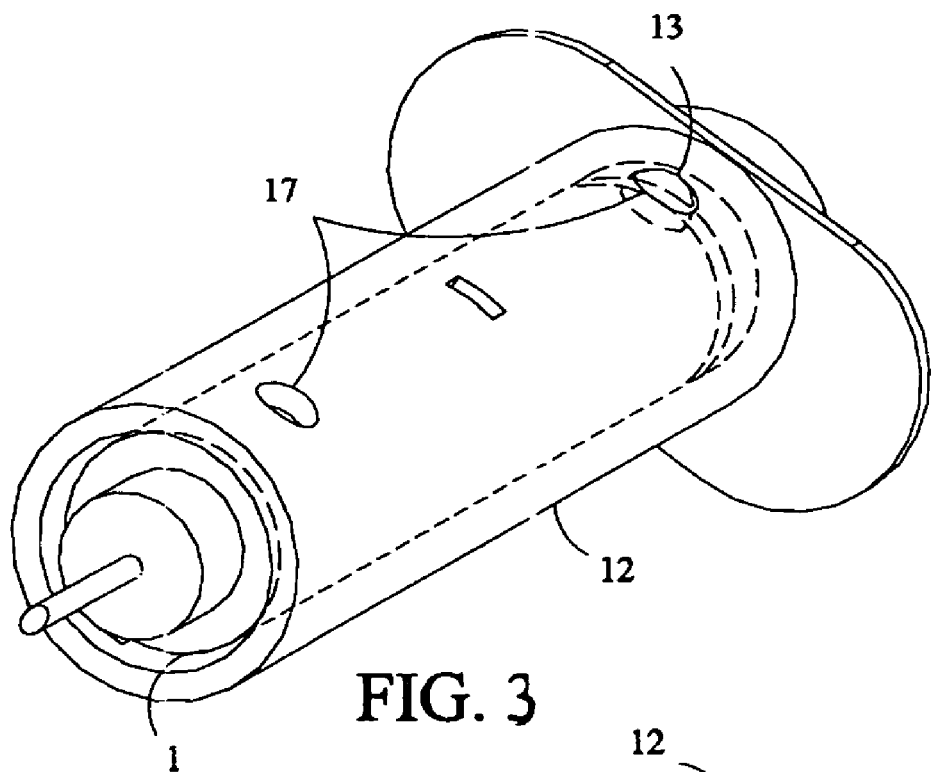
FIG. 3 is a perspective view of the syringe in its initial state.

Shown in FIG. 3, is the initial state of the syringe, with caps removed. Retaining hole 17 is latched over the retaining detent 13 of the anti-needlestick 12 around the barrel 1.

Figure 3A:
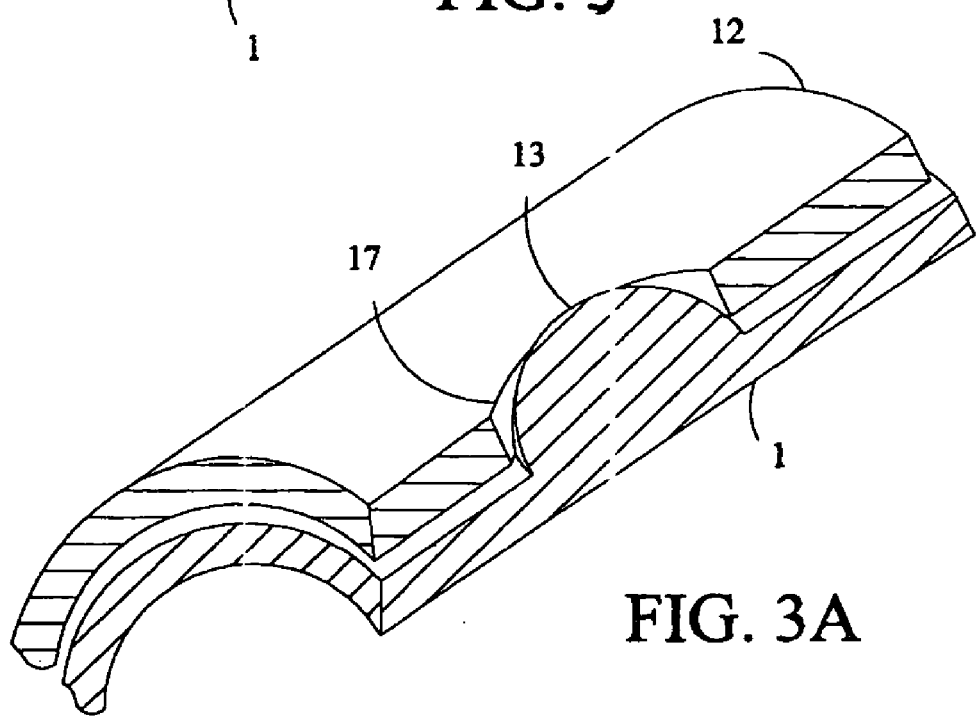
FIG. 3A is a close-up cross sectional view of the retaining detent on the barrel and mating retaining hole in the anti-needlestick sleeve.

Close-up cross section view provided by FIG. 3A shows the anti-needlestick sleeve 12 positioned such that its retaining hole 17 fits over the retaining detent 13 on the barrel 1. When the sleeve 12 is manually squeezed, it alters its shape enough that the retaining hole 17 is released from the retaining detent 13.

Figure 4:
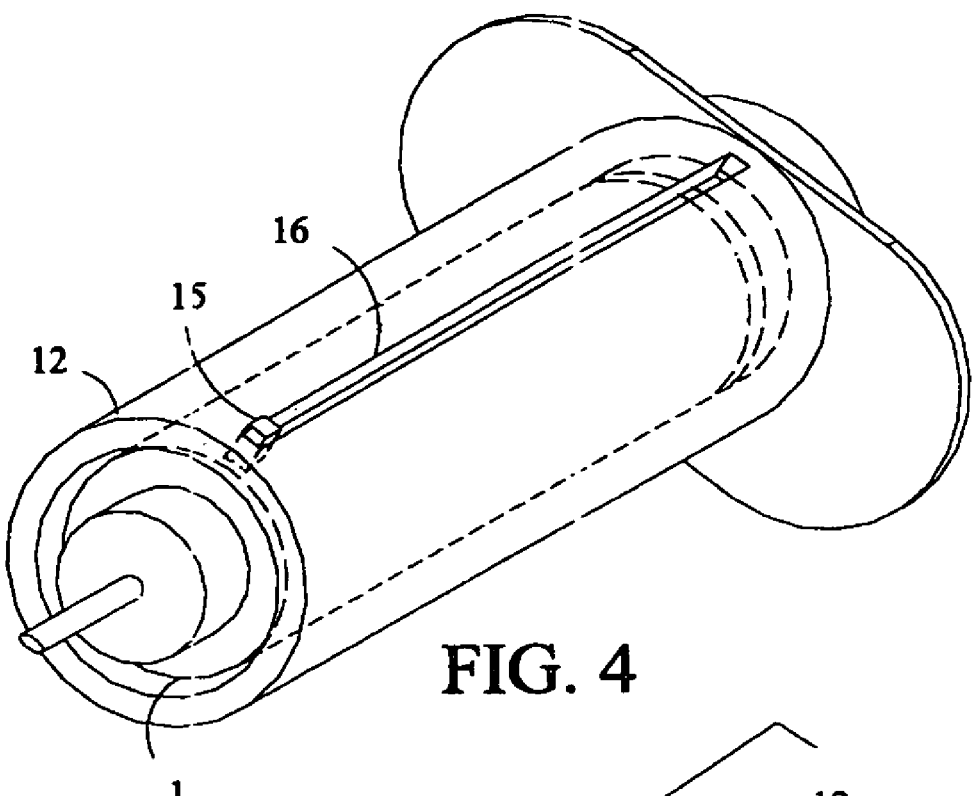
FIG. 4 is a perspective rear view of the syringe in its initial state.
Figure 4A:
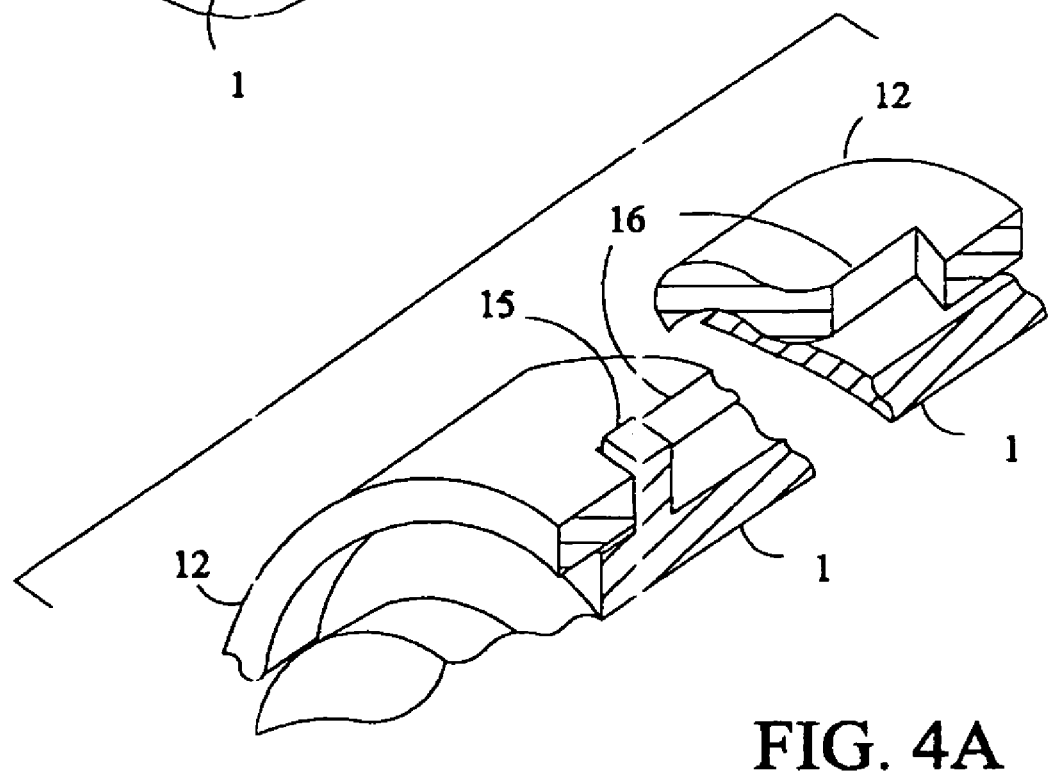
FIG. 4A is a close up cross sectional view of the guide detent on the barrel and the guiding slot in the anti-needlestick sleeve.

Shown in FIG. 4 and FIG. 4A, the guide slot 16 on the sleeve 12 assures its longitudinal movement along the guide detent 15 on the barrel 1.

Figure 5:
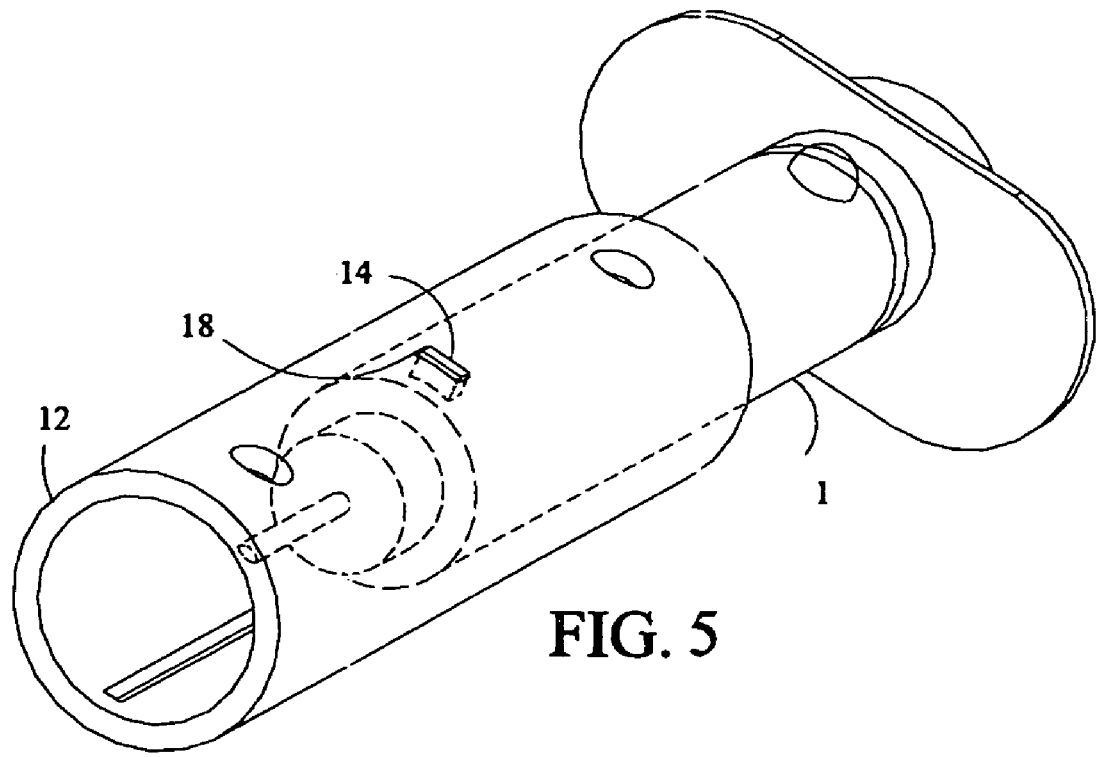
FIG. 5 is a front view of the syringe in its final state with the anti-needlestick sleeve fully deployed.

As shown in FIG. 5, the sleeve 12 can then be slid in a downward direction (which is opposite to the direction which might cause an accidental needlestick) until its latching hole 18 reaches the latching detent 14 on the barrel 1 onto which it latches.

Figure 5A:
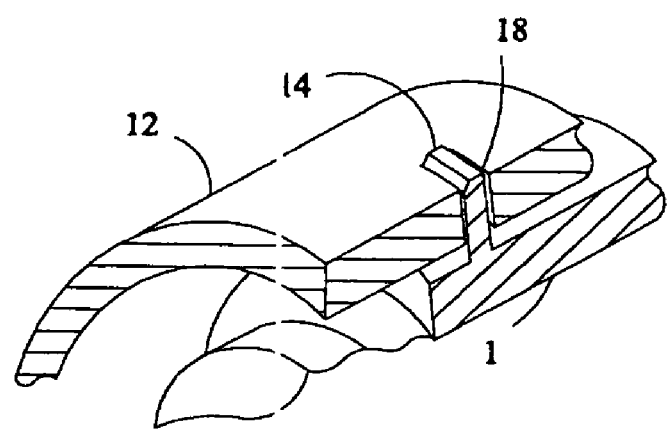
FIG. 5A is a close-up cross sectional view of the latching detent on the barrel engaged with the latching hole in the anti-needlestick sleeve.

Shown in FIG. 5A is a close-up cross-section view of latching hole 18 on the anti-needlestick sleeve 12 and the latching detent 14 on the barrel 1.

This is the final state of the syringe when the anti-needlestick sleeve has been fully deployed. While only one retaining hole is required for function, to facilitate ease of assembly the anti-needlestick sleeve can be constructed symmetrically with the latching hole centrally located and two identical retaining holes placed near each end of the sleeve, thus making the sleeve reversible. The purpose of the anti-needlestick sleeve is to shield the user or other handlers from the needle after the use of the syringe, thereby reducing needlestick accidents.

Figure 6:
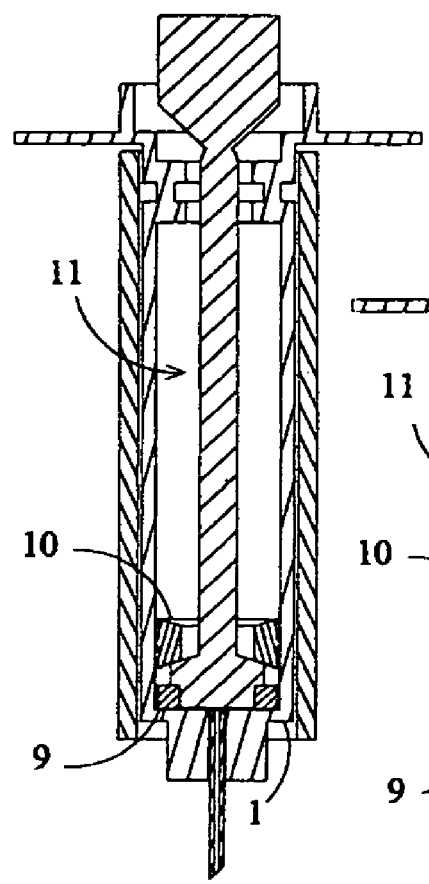
FIG. 6 through FIG. 6E illustrates the operational steps of the use of the syringe.

Operation of the syringe. To use the syringe, the user first removes and discards the plunger cap to expose the plunger handle 7, and then removes the needle cap and discards it to expose the needle. FIG. 6 through FIG. 6E are cross sectional views that show how the syringe can be used only once, and is then rendered completely non-reusable. Shown in FIG. 6 is the syringe as shipped to the user in an initial state, such that the lower seal 9, the plunger 11, and the upper seal 10 (together hereafter referred to as the plunger assembly) are all fully pushed down to the bottom of the barrel 1 and are in contact with each other. The user then inserts the needle into the location from which the liquid is to be drawn, such as, but not limited to, a medicine vial.

Figure 6A:
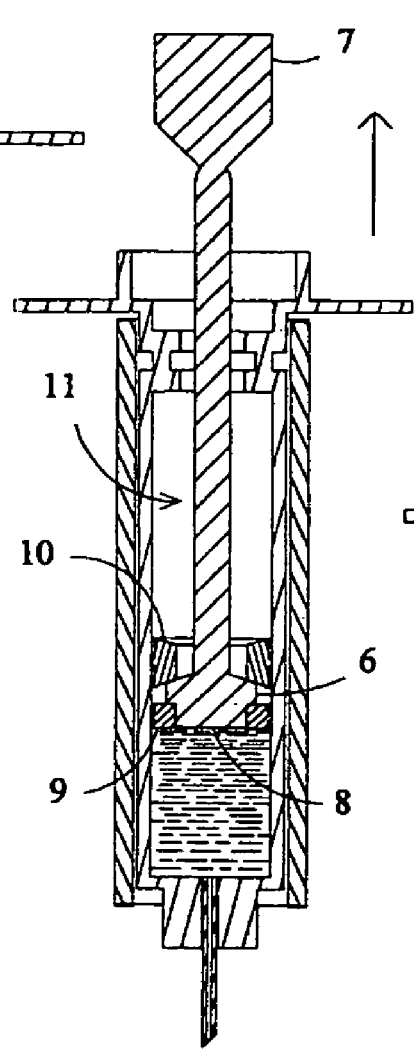
Figure 6B:
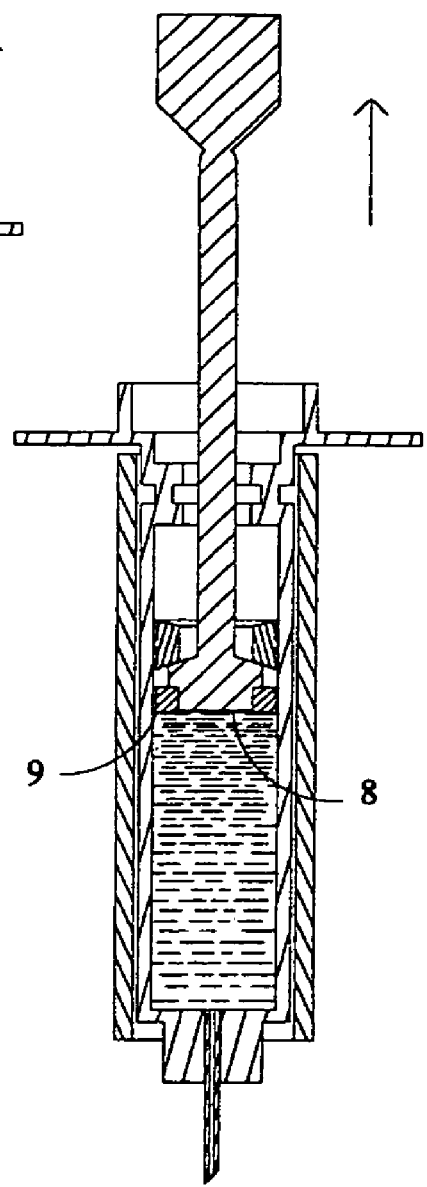

As shown in FIG. 6A, the user next pulls the plunger handle 7. As the user does so, a primary partial vacuum is created between the lower seal 9 and the upper seal 10. As the upper seal 10, which rides atop the spider 6, is pulled upward through the barrel by the mechanical action of pulling the plunger handle 7, the lower seal 9 is forced to follow the plunger 11 and the upper seal 10 by the vacuum force between the two seals. This movement creates a secondary partial vacuum below the plunger assembly, which in turn draws liquid into the syringe through the needle, as is typical in most syringes. This plunger retraction continues until the syringe has sufficient medicament for the injection. The needle is then withdrawn from the vial. It is important to note that the lower seal 9 forms a slip fit with the stem extension 8 and air-tight fit with the barrel wall and moves in tandem with the spider 6 not because of solid mechanical coupling with the spider 6 or with the stem extension 8, but because of the mechanically induced primary partial vacuum created between the upper seal 10 and lower seal 9.

Figure 6C:
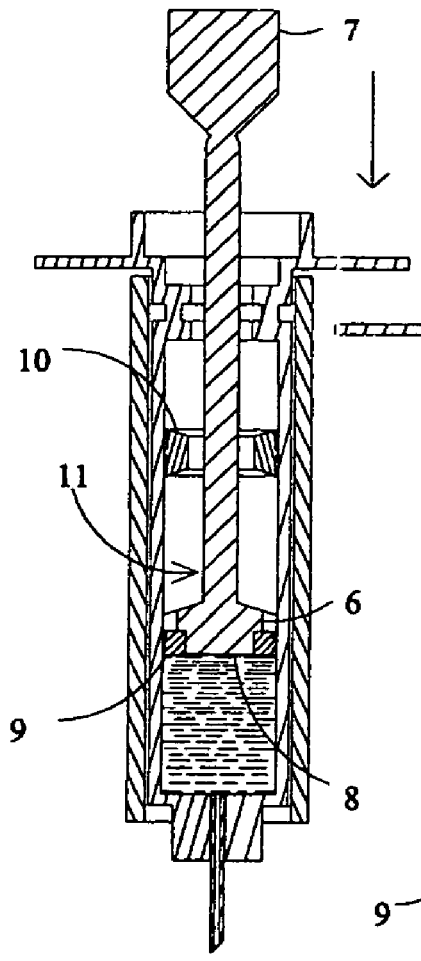

As seen in FIG. 6C, when the liquid is to be injected into the patient, the syringe can be purged of any air and the exact dosage can be set by the common practice of inverting the syringe and compressing the plunger handle 7. The needle is then inserted into the injection site. The plunger 11 is pushed in by applying pressure on the handle 7. This reversal of the plunger direction separates the upper seal 10 from the spider, and therefore irretrievably interrupts the primary partial vacuum between the upper seal 10 and the lower seal 9. This action forces the spider 6 downward, against the lower seal 9, thus maintaining the liquid-tight fit between the inner wall of the lower seal 9 and the outer wall of the stem extension 8.

Figure 6D:
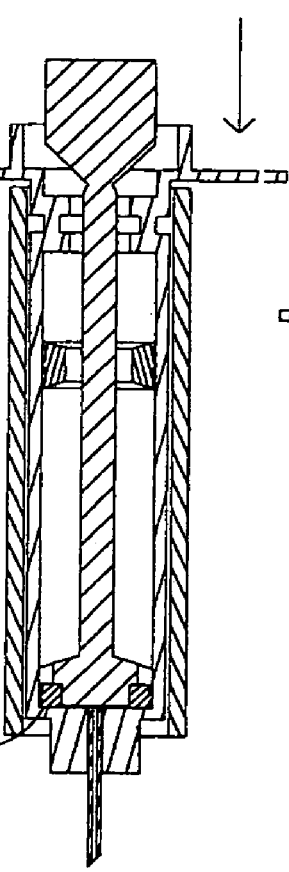
Figure 6E:
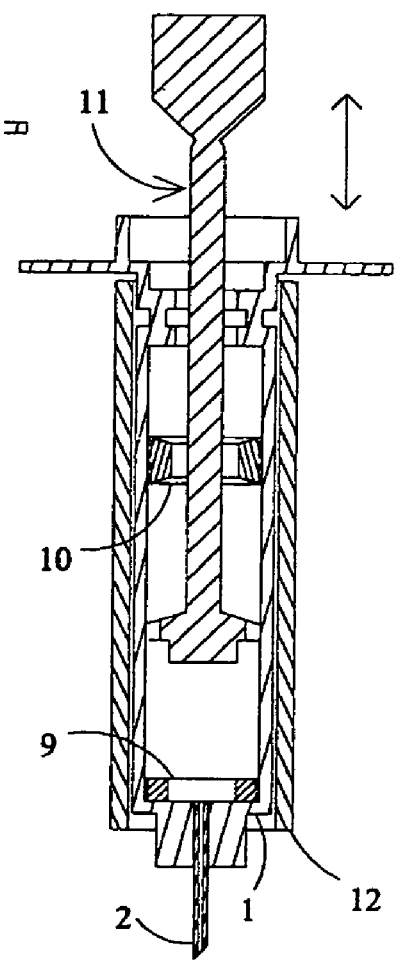

Shown in FIG. 6D, continued pushing of the plunger until the lower seal 9 is at the bottom of the barrel and all liquid is ejected from the syringe, completes the injection. At this point, the user extracts the needle from the injection site.

As shown in FIG. 6E, the syringe is now rendered completely non-reusable. The upper seal 10 is irretrievably abandoned in the upper barrel and the lower seal 9 is irretrievably abandoned in the bottom of the barrel. Any attempt to pull the plunger 11 to form a vacuum will dislodge the stem extension 8 from the lower seal 9, abandoning the lower seal 9 in the bottom of the barrel 1. Any attempt to refill the syringe 20 from a pressurized vial will fail as the liquid will enter the bottom of the barrel 1, flow past the abandoned lower seal 9 and become lost in the syringe 20 with no means available for its expulsion back through the needle 2. This renders the syringe completely non-reusable.

All seals essential to the operation of the syringe are now rendered non-functional. If a pressurized liquid is reintroduced into the syringe, it will bypass the abandoned lower seal and thus become non-ejectable. This means that the syringe cannot be used more than once. It can be safely disposed of, in the normal waste stream, without fear of it being reused. The non-reuse function is now complete.

As was seen in FIGS. 3, 4 and 5, the anti-needlestick function now begins. After the injection, the user squeezes the anti-needlestick sleeve 12 slightly to release it from its loosely held grip with the retaining detent 13 and slides it forward until it latches onto the latching detent 14, to prevent accidental needle sticking.

Shown in FIG. 5 and FIG. 6E, the non-reuse feature is in effect and the needle is shielded so that the syringe can now be safely discarded. This is the final state of the syringe.

It may be possible for someone to defeat the non-reusability feature of the syringe by cutting the barrel open to tamper with its mechanism. As an additional precaution against such tampering, the barrel can be constructed from a tempered material that would shatter when any attempt is made to penetrate it. Such materials include, but are not limited to, a variety of thermoplastics and glass.

Additionally, removal of the needle from the barrel for intravenous drug abuse purposes can be thwarted by annealing the top of the needle (where it is molded into the barrel) before the insertion molding process. Attempts to remove the needle from the barrel would result in the needle collapsing and thus becoming useless.

While the above description contains many specificities, the reader should not construe these as limitations on the scope of the invention, but merely as examples of preferred embodiments thereof. Those skilled in the art may envision many other possible variations within its scope. Accordingly, the reader is requested to determine the scope of the invention by the appended claims and their legal equivalents, and not solely by the given examples.

What is claimed is:

1. A disposable syringe incapable of re-use regardless of the user's intent comprising:
 a barrel in the shape of a hollow cylinder, having its upper end open and equipped on the outside with finger gripping devices positioned and shaped to be gripped with two fingers for better handling, and terminated at its lower end with a needle cap holding a medical injection needle;
 a plunger in slidable contact with the inside surface of said barrel, said plunger
 comprising:
  i. an elongated stem substantially concentric with said barrel;
  ii. a disk called a "spider" held by said stem near the lower end of said stem, said spider perpendicular to the axis of, and axially centered with, said stem, at least one gap existing between said spider and said barrel, said gap called spider gap, wherein said spider gaps are formed by at least two indentations located at the periphery of said spider, periphery of said spider between indentations forming a loose fit with inner wall of said barrel;
  iii. a stem extension in the shape of a short cylinder of predetermined length and diameter, affixed to the lower face of said spider and axially centered with said stem, and
  iv. a handle affixed to upper end of said stem;
 a lower seal of cylindrical annular shape made of rubbery material, having its external cylindrical surface forming an air-tight fit with inner wall of said barrel, and having its internal cylindrical surface forming a liquid-tight slip fit with said stem extension, and furthermore having its upper surface conform to lower surface of said spider thereby forming when said spider and said lower seal are in contact, a liquid-tight combination henceforth called lower liquid-tight combination; and
 an upper seal of cylindrical annular shape made of rubbery material, having its external cylindrical surface forming an air-tight fit with inner wall of said barrel, and having its internal diameter larger than said stem, thereby forming a gap between said upper seal and said stem, said gap allowing fluid to circulate freely, and furthermore having its lower surface conform to upper surface of said spider, thereby, forming when said spider and said upper seal are in contact, an air tight combination henceforth called upper air-tight combination;
 the initial state of said syringe being such that said lower seal, said plunger and said upper seal are all located all the way, down said barrel forming said lower liquid-tight combination and said upper air-tight combination,
 whereby,
 upon first use of said syringe, when said plunger is pulled up thus drawing up said spider, said spider pulling said upper seal upward thereby creating a primary vacuum below said upper seal, and above said lower seal, said primary vacuum pulling said lower seal upward, thereby drawing liquid into said syringe, and
 upon first use of said syringe, when plunger is pushed downward, said spider is also pushed downward, thereby pushing down said lower seal downward and expelling said liquid from said syringe until said spider and said lower seal reach the bottom of said syringe, and furthermore, abandoning said upper seal near the top of said barrel,
 said syringe becomes unusable for any subsequent use because said upper seal is abandoned near the top of said barrel, primary partial vacuum cannot be formed again, and said spider gaps preventing said spider from operating as a piston in said syringe, thereby preventing said lower seal to be drawn upward by pulling on said plunger.

2. A syringe as in claim 1 wherein said upper seal and said lower seal carry ribs on their outer surface in contact with the inner wall of said barrel, the number of said ribs being used to control the amount of friction said upper seal and said lower seal have with the inner wall of said barrel.

3. A syringe as in claim 2 wherein said ribs are different in their cross section shape.

4. A syringe as in claim 2 wherein a slant in said cross section shape is generated by the frictional force between said ribs and inner wall of said barrel, said slant producing a sharp increase in frictional force upon a change in the direction of motion of said plunger, said sharp increase in frictional force facilitating said abandonment of said upper seal.

5. A syringe as in claim 4 wherein stem extension is shorter than said lower seal by an interval ranging from 0.002 inches to 0.020 inches.

6. A syringe as in claim 1 also comprising an anti-needlestick sleeve in essentially the shape of a hollow cylindrical body made of flexible transparent material loosely fitting over said barrel, and which can be slid from a retracted position to an extended position, said anti-needlestick sleeve comprising:
 a. at least one retaining hole cut in said cylindrical body;
 b. a guide slot cut in said cylindrical body longitudinal direction, and
 c. a latching hole cut in said cylindrical body; and
 said barrel comprising on its outer surface:
 a. a retaining detent matching in location said retaining hole when said anti-needlestick sleeve is in a retracted position;
 b. a guide detent matching in location said guide slot, and
 c. a latching detent, matching in location said latching hole when said anti-needlestick sleeve is in an extended position,
 combination of said retaining detent and retaining hole keeping said anti-needlestick sleeve in said retracted position before and during use, thereby exposing said needle,
 flexibility of said anti-needlestick sleeve allowing it to be compressed from a circular cylindrical shape to an oval cylindrical shape thereby allowing the release of said retaining hole from said retaining detent by the application of sideways pressure,
 combination of said guide detent and guide slot constraining the movement of said anti-needlestick sleeve to a longitudinal direction with respect to said syringe, and allowing said anti-needlestick sleeve to be slid from said retracted position to said extended position thereby shielding said needle,
 combination of said latching hole and said latching detent keeping said anti-needlestick sleeve in a permanent extended latched position after use, thereby shielding said needle and preventing it from being exposed again.

7. A syringe as in claim 6 wherein said anti-needlestick sleeve is 180 degrees reversible with respect to the axis of said syringe, and with respect to said retaining hole, said guide slot and said latching hole, thereby facilitating assembly.

8. A syringe as in claim 6 wherein said retaining detent is cabochon shaped.

9. A syringe as in claim 6 wherein said latching detent is rectangular in cross section.

10. A syringe as in claim 1 wherein said plunger comprises a single molded piece that includes said stem and an element selected from the group consisting of said spider, said stem extension, said handle and combinations thereof.

11. A syringe as in claim 1 wherein said spider carries indentations on its periphery.

12. A syringe as in claim 1 wherein said lower seal and said upper seal are 180 degrees reversible in orientation with respect to the axis of said syringe, thereby facilitating the manufacturing of said syringe.

13. A syringe as in claim 1 wherein said lower seal and said upper seal are identical.

14. A syringe as in claim 1 wherein said stem extension is shorter than said lower seal.

15. A syringe as in claim 1 wherein said barrel is made of material conductive to light.

16. A syringe as in claim 1 wherein said barrel is made of a tempered material.

17. A syringe as in claim 1 wherein said needle is annealed at its base.

18. A syringe as in claim 1 wherein said handle is manufactured by forming a billet in upper end of said stem, inserting said upper seal and flattening said billet into a flat flexible handle.

19. A syringe as in claim 1 wherein said handle is manufactured by affixing a flat disc button at the upper end of said stem, said button being perpendicular to the axis of said syringe.

20. A syringe as in claim 1 wherein upper end of said barrel is crimped, thereby preventing tampering with said upper seal, said lower seal or said plunger.

21. A syringe as in claim 1 wherein a vacuum is established at manufacturing time between said lower seal and said upper seal.

* * * * *